US00PP33784P2

(12) United States Plant Patent
Jelenkovic et al.

(10) Patent No.: US PP33,784 P2
(45) Date of Patent: Dec. 28, 2021

(54) STRAWBERRY PLANT NAMED 'NJ09-2-1'

(50) Latin Name: *Fragaria ananassa*
Varietal Denomination: NJ09-2-1

(71) Applicant: RUTGERS, THE STATE UNIVERSITY OF NEW JERSEY, New Brunswick, NJ (US)

(72) Inventors: Gojko L Jelenkovic, Piscataway, NJ (US); Peter J. Nitzsche, Morristown, NJ (US); William T Hlubik, Bordentown, NJ (US); Matthew Milburn, Milltown, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 0 days.

(21) Appl. No.: 17/157,349

(22) Filed: Jan. 25, 2021

(51) Int. Cl.
*A01H 5/08* (2018.01)
*A01H 6/74* (2018.01)

(52) U.S. Cl.
USPC ..... Plt./208

(58) Field of Classification Search
USPC ..... Plt./208, 209
See application file for complete search history.

*Primary Examiner* — Susan McCormick Ewoldt
(74) *Attorney, Agent, or Firm* — Patrick J. Daugherty; Daugherty & Del Zoppo Co. LPA

(57) ABSTRACT

A new and distinct strawberry plant variety of *Fragaria ananassa* named 'NJ09-2-1' is provided, a short day cultivar primarily adapted to the climate and conditions of the eastern United States (USDA Plant Hardiness Zones 5b, 6a 6b, 7a, 7b, 8a and 8b). 'NJ09-2-1' has large, long conic to cylindrically shaped fruit, with a medium glossy even surface, a raised calyx with upward sepals, and a medium to broad band without achenes.

4 Drawing Sheets

Latin name of genus and species of the plant claimed: *Fragaria ananassa.*

Variety denomination: 'NJ09-2-1'.

BACKGROUND OF THE INVENTION

The present invention relates to a new and distinct variety of strawberry plant named 'NJ09-2-1' that resulted from a controlled cross between the female parent 'NJ6-13-1' (unpatented) and the male parent 'NJ03-232-2' (unpatented) in 2009. Both parental genotypes are derivatives of many cycles of crosses and selection, 'NJ6-13-1' was chosen for its large fruit size. 'NJ03-232-2' was chosen for the excellent flavor of its fruit. Seeds of the cross were germinated in a greenhouse and planted in the field at a research farm in New Brunswick, N.J. in 2010. Plants were evaluated for two seasons in observational plots. The selected plant designated as 'NJ09-2-1' was recognized for its vigor, productivity, and large flavorful fruit. After its selection, 'NJ09-2-1' was asexually propagated using stolons for further evaluations in observational and replicated trials in New Jersey and Pennsylvania from 2013 to 2018. 'NJ09-2-1' as herein described and illustrated was found to remain true to type through successive generations of asexual production.

BRIEF SUMMARY OF THE INVENTION

'NJ09-2-1' is a short day cultivar primarily adapted to the climate and conditions of the eastern United States (USDA Plant Hardiness Zones 5b, 6a 6b, 7a, 7b, 8a and 8b.

'NJ09-2-1' has large, long conic to cylindrically shaped fruit, with a medium glossy even surface, a raised calyx with upward sepals, and a medium to broad band without achenes.

'NJ09-2-1' is believed to be most closely related to the strawberry variety 'NJ08-08-6' (U.S. Plant Pat. No. 27,544) with which it shares the pollen parent 'NJ03 232 2' (unpatented). Flowering 'NJ09-2-1' and 'NJ08-08-6' plants can easily be distinguished by the attitude of their pedicel hair (upwards and horizontal, respectively). 'NJ09-2-1' and 'NJ08-08-6' fruit differ in size and shape, including as discussed below in the detailed botanical description.

'NJ09-2-1' fruit is generally larger and heavier than that of 'NJ08-08-6'. The shape of 'NJ09-2-1' fruit ranges from long conic to cylindrical, while 'NJ08-08-6' fruit is conical. Both 'NJ09-2-1' and 'NJ08-08-6' fruit have excellent flavor. No representations are made with regard to greater resistance or lessened susceptibility to pests or diseases in comparison to 'NJ08-08-6'.

Figure 1:
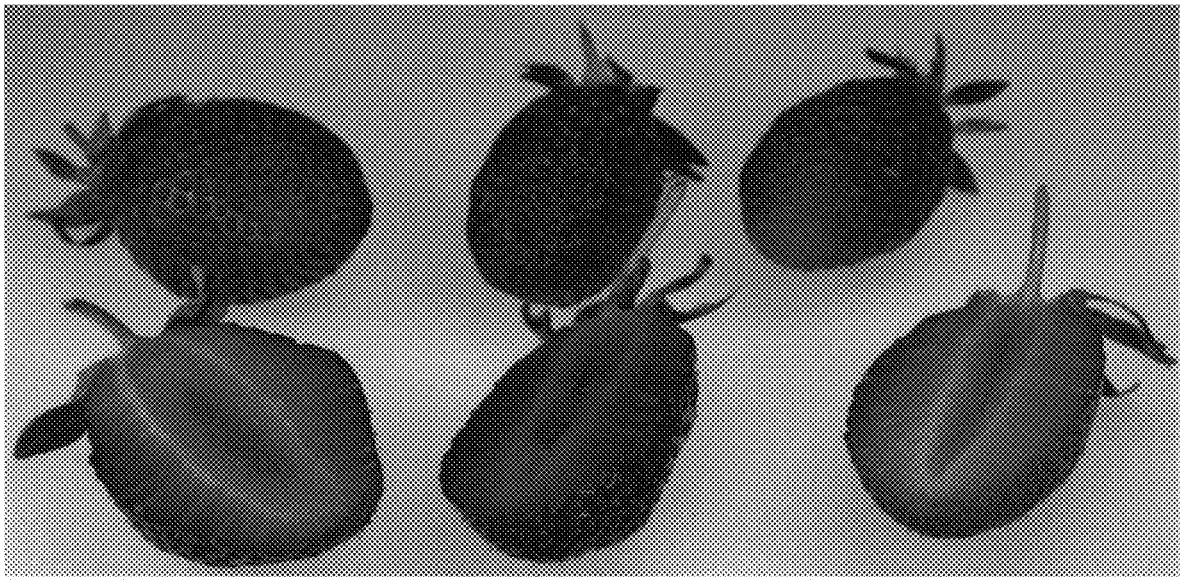
FIG. 1 is a color photograph showing a long conic to cylindrical shape of a 'NJ09-2-1' fruit. The sepals of ripe 'NJ09-2-1' fruit are usually pointed upright.
Figure 2:
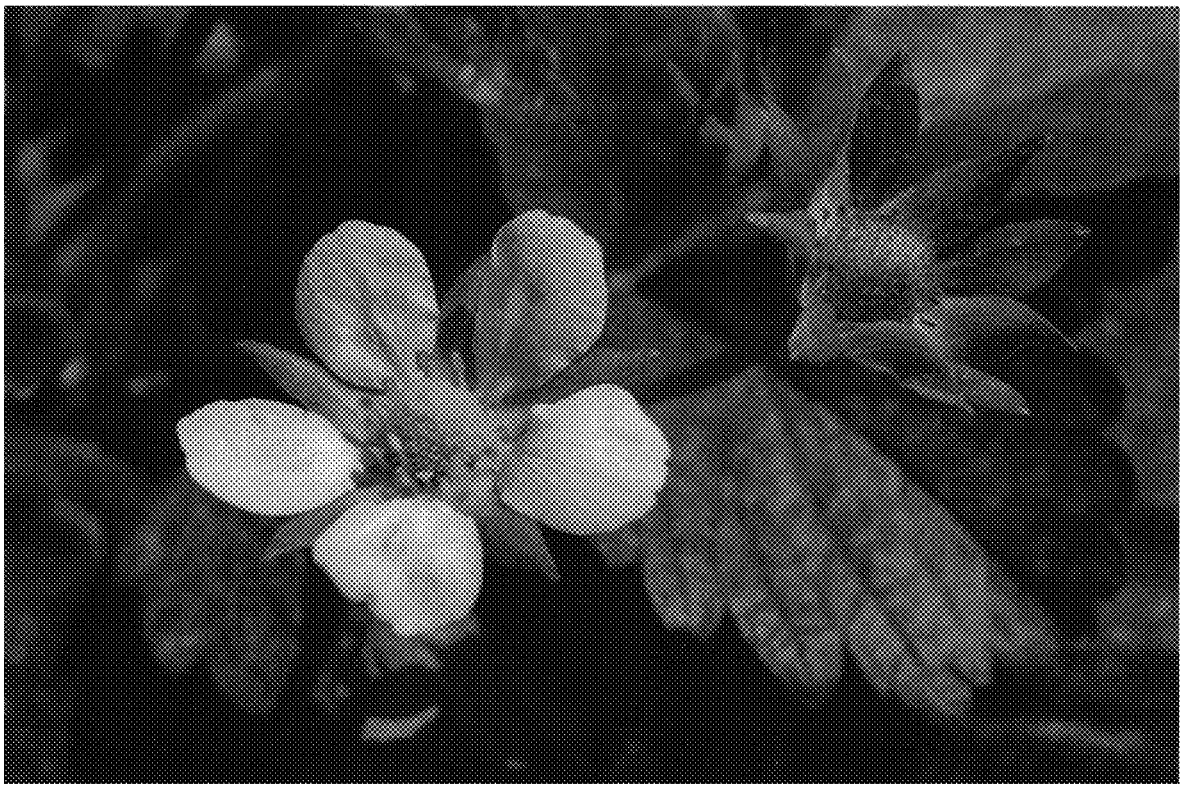
FIG. 2 is a color photograph showing a 'NJ09-2-1' flower.
Figure 3:
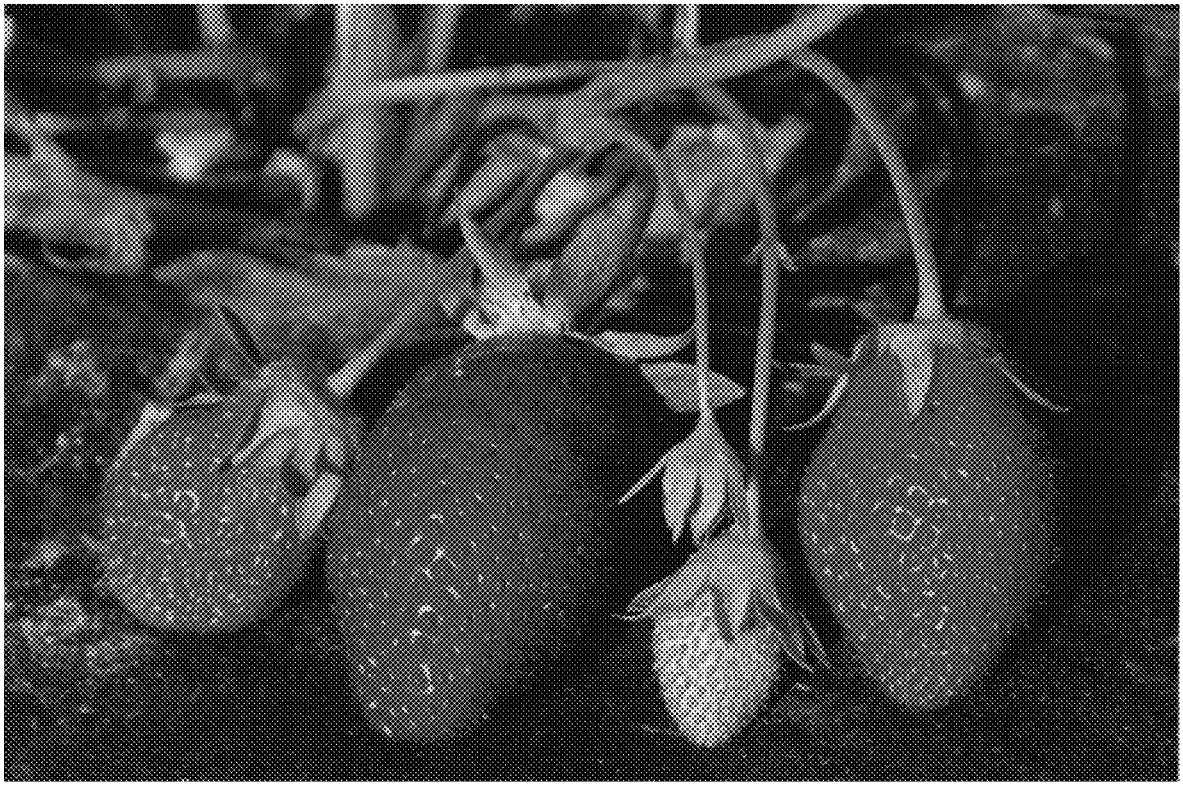
FIG. 3 is a color photograph showing a 'NJ09-2-1' fruit cluster.
Figure 4:
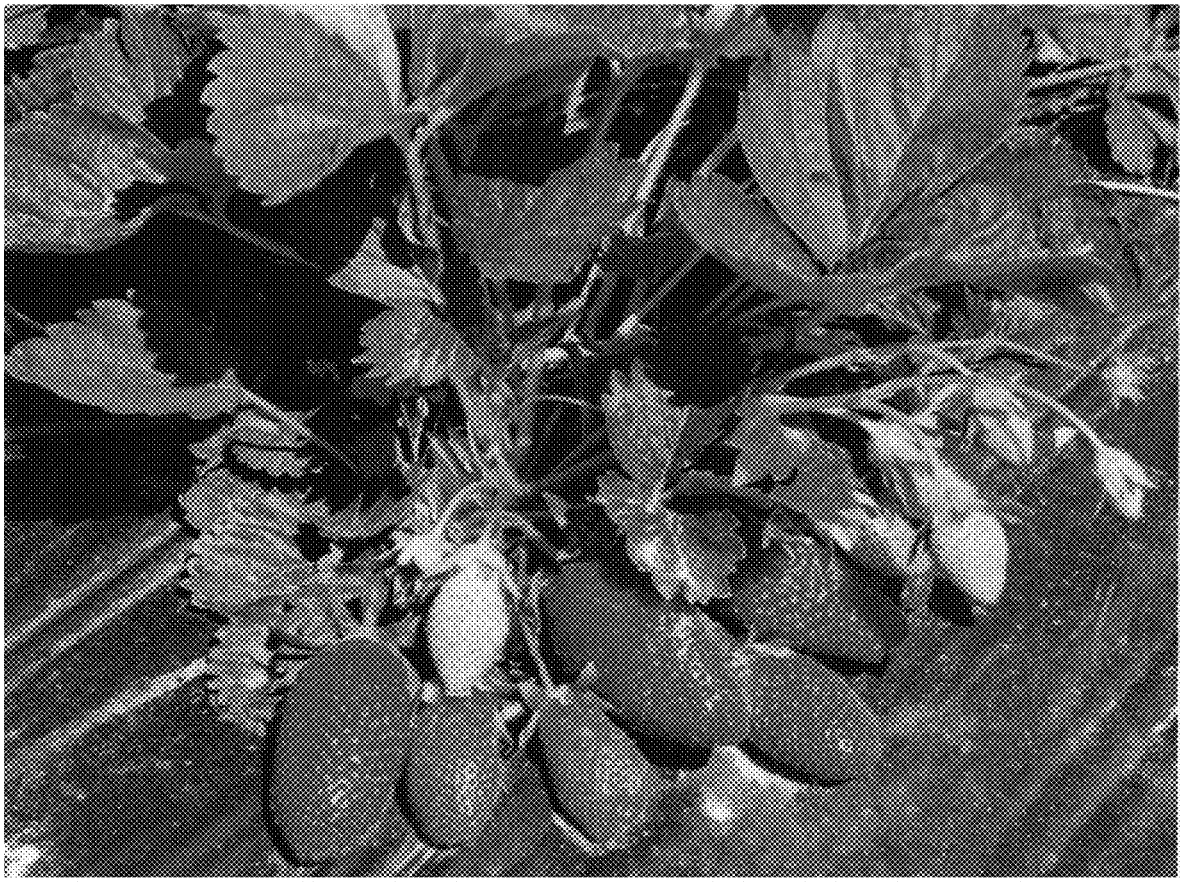
FIG. 4 is a color photograph showing a 'NJ09-2-1' whole plant with fruit.

Colors are approximate as color depends on horticultural practices, such as light level, fertilization rate, and other conditions; colors of and illustration of this type may also vary with lighting and other conditions. Therefore, color characteristics of this new variety should be determined with reference to the observations described herein, rather than from these illustrations alone.

DETAILED BOTANICAL DESCRIPTION

'NJ09-2-1' is associated with Rutgers D'Light™, a trademark of Rutgers, The State University of New Jersey, in the United States or other countries.

Color references are to the *The Royal Horticultural Society Colour Chart* (R.H.S. 5th Ed. 2007).

Colors of foliage, flowers and fruit may vary with the age of the plant part, and variations in abiotic conditions.

Fruit characteristics:

*Color of mature fruit*.—Slightly uneven. Color predominantly between RHS 45A and 53A (red); below the calyx, the color of a band without achenes is between NN155B and 43A (white to red).
*Color of internal flesh*.—RHS 45A (red).
*Color of core*.—RHS 44B (red).
*Fruit cavity*.—Absent or small.
*Predominant shape*.—Long conic to cylindrical.
*Difference in shape between primary and secondary fruit*.—Slight.
*Average length (cm)*.—4.6.
*Average width (cm)*.—3.1.
*Average weight (grams)*.—20.
*Average length/width ratio*.—1.5.
*Achene color*.—RHS 152C (yellow-green).
*Average number of achenes per berry*.—220.
*Position of achenes*.—Below to level with surface.
*Width of band without achenes*.—Medium to broad.
*Evenness of surface*.—Even.
*Glossiness*.—Medium.
*Diameter of calyx in relation to diameter of fruit*.—Slightly larger.
*Position of calyx attachment*.—Raised.
*Attitude of sepals*.—Variable.
*Adherence of calyx (when fully ripe)*.—Strong.
*Firmness of flesh*.—Firm.
*Flavor*.—Good.
*Average soluble solids concentration*.—8.7% Brix, ranging from 7.6% to 10.4% (as discussed below in comparison to 'NJ08-08-6' and 'Chandler' (U.S. Plant Pat. No. 5,262).
*Type of bearing*.—Short day, not remontant.
*Time of first flowering*.—Early May in USDA Plant Hardiness Zone 6b.
*Time of first harvesting*.—Late May in USDA Plant Hardiness Zone 6b.
*Harvest period*.—3 weeks.

Plant characteristics:

*Growth habit*.—Semi-upright.
*Density of foliage*.—Medium.
*Vigor*.—Medium.
*Position of inflorescence in relation to foliage*.—Beneath to same level.
*Fruit truss average length at maturity*.—15 cm., from the base of the truss deep in the crown to the base of primary fruit calyx.
*Fruiting truss average diameter at base*.—0.4 cm.
*Fruit truss density of pubescence*.—Sparse.
*Number of stolons*.—Medium, average of 5 per crown.
*Stolon average diameter at bract*.—0.4 cm.
*Stolon anthocyanin coloration*.—Medium.
*Stolon density of pubescence*.—Sparse.

Foliage characteristics:

*Leaf blistering*.—Medium.
*Leaf glossiness*.—Medium.
*Leaf variegation*.—Absent.
*Color of leaf upper surface*.—RHS N137B (green) to 147A (yellow-green).
*Color of leaf underside*.—RHS 147B (yellow-green).
*Number of leaflets per leaf*.—3.
*Terminal leaflet average length*.—9.5 cm.
*Terminal leaflet average width*.—8.4 cm.
*Terminal leaflet average length/width ratio*.—1.1.
*Terminal leaflet shape in cross section*.—Concave.
*Terminal leaflet shape of base*.—Obtuse to rounded.
*Terminal leaflet shape of margin*.—Serrate to crenate.
*Terminal leaflet average number of serrations*.—22.
*Color of terminal leaflet petiolule*.—RHS 146D (yellow-green).
*Terminal leaflet petiolule average length*.—1.3 cm.
*Terminal leaflet petiolule average diameter*.—0.2 cm.
*Terminal leaflet petiolule pubescence*.—Medium, attitude of hair: upwards and outwards.
*Color of petiole*.—146D (yellow-green).
*Petiole length*.—Medium to long, average 19 cm, with range of 12 cm to 25 cm.
*Petiole diameter*.—0.5 cm.
*Petiole pubescence*.—Sparse.
*Stipule anthocyanin coloration*.—Weak, colored edges with an orange-red color with varying intensity from N34A to N34C.
*Stipule average length*.—3.3 cm.
*Stipule average width*.—0.7 cm.
*Stipule pubescence*.—Absent.

Flower characteristics:

*Petal color*.—Upper surface RHS 155B (white).
*Sepal color*.—Upper surface RHS 141A (green).
*Corolla average diameter*.—33 mm.
*Calyx average diameter*.—27 mm.
*Petal average length*.—14 mm.
*Petal average width*.—12 mm.
*Petal average length/width ratio*.—1.2.
*Petals/flower*.—5.
*Sepal average length*.—10 mm.
*Sepal average width*.—4 mm.
*Sepal average length/width ratio*.—2.5.
*Sepals/flower*.—10.
*Relative position of petals*.—Free.
*Stamen*.—Present.
*Pedicel attitude of hairs*.—Upwards.
*Average number of flowers/plant*.—41, ranging from 28 to 53 flowers per plant in early May.

Comparison: The flowing observations compare the fruit characteristics of 'NJ09-2-1' to the closely-related 'NJ08-08-6' variety, and the 'Chandler' variety which is commonly grown in the eastern United States.

*Shape*.—'NJ09-2-1' is long conic to cylindrical, 'NJ08-08-6' is conical; 'Chandler' is conical to wedged.
*Calyx attachment*.—'NJ09-2-1' is raised, 'NJ08-08-6' is raised; 'Chandler' is level.
*Diameter of calyx in relation to diameter of fruit*.—'NJ09-2-1' is slightly larger; 'NJ08-08-6' is slightly smaller; and 'Chandler' is same size.
*Width of band without achenes*.—Medium to broad for 'NJ09-2-1'; narrow for 'NJ08-08-6'; absent or very narrow for 'Chandler'.
*Weighted average fruit weight ranges, in grams/fruit*.—17.5-22.0 for 'NJ09-2-1'; 14.3-16.8 for 'NJ08-08-6'; and 15.0-19.2 for 'Chandler'. The weighted average fruit weight range values were observed in five trials conducted in New Jersey between 2014 and 2018, wherein the 'NJ08-08-6' was not present in the 2018 trial. The weighted average fruit weight is the total marketable yield (including primary, secondary, and tertiary fruit) divided by the total number of fruits harvested per plot. Total number of fruit harvested per plot was estimated by dividing marketable yield by the average fruit weight (determined on a sample of 20 fruit, or on all fruit if fewer than 20 present) for each harvest, and summing the number of fruit for all harvests.

*Range of average brix value percentages.*—7.6-10.4 for 'NJ09-2-1' 7.5-9.6 for 'NJ08-08-6'; and 7.0-8.5 for 'Chandler'. The average Brix values were observed in live trials conducted in New Jersey between 2014 and 2018, wherein 'NJ08 08 6' was not present in the 2018 trial, and the Brix values were determined on live fruit per variety at three or four harvests.

We claim:

1. A new and distinct variety of strawberry plant named 'NJ09-2-1', substantially as herein shown and described.

* * * * *